(12) United States Patent
Voisard et al.

(10) Patent No.: US 9,107,752 B2
(45) Date of Patent: *Aug. 18, 2015

(54) COATED IMPLANT

(71) Applicant: DePuy Synthes Products, Inc., Raynham, MA (US)

(72) Inventors: Cyril Voisard, Oberdorf (CH); Goetz Thorwarth, Oberdorf (CH); Markus Kraft, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/920,310

(22) Filed: Jun. 18, 2013

(65) Prior Publication Data
US 2013/0282137 A1    Oct. 24, 2013

Related U.S. Application Data

(63) Continuation of application No. 13/166,898, filed on Jun. 23, 2011, now Pat. No. 8,486,152.

(60) Provisional application No. 61/358,968, filed on Jun. 28, 2010.

(51) Int. Cl.
*A61F 2/28* (2006.01)
*A61K 6/083* (2006.01)
(Continued)

(52) U.S. Cl.
CPC ............... *A61F 2/28* (2013.01); *A61F 2/3094* (2013.01); *A61F 2/30767* (2013.01); *A61F 2/442* (2013.01); *A61L 27/04* (2013.01); *A61L 27/303* (2013.01); *A61L 27/34* (2013.01); *A61F 2002/30014* (2013.01); *A61F 2002/30016* (2013.01); *A61F 2002/30166* (2013.01); *A61F 2002/30324* (2013.01); *A61F 2002/30563* (2013.01); *A61F 2002/30884* (2013.01); *A61F 2002/30929* (2013.01); *A61F 2310/0055* (2013.01); *A61F 2310/0058* (2013.01); *A61F 2310/00407* (2013.01); *A61F 2310/00413* (2013.01); *A61F 2310/00491* (2013.01);
(Continued)

(58) Field of Classification Search
None
See application file for complete search history.

(56) References Cited

U.S. PATENT DOCUMENTS 6,761,736 B1 * 7/2004 Woo et al. ............... 623/2.42
7,291,173 B2 * 11/2007 Richelsoph et al. ....... 623/17.13
(Continued)

FOREIGN PATENT DOCUMENTS

CN    1764425 A    4/2006
EP    1754684      2/2007
(Continued)

OTHER PUBLICATIONS

Kiuru et al., "Tantalum as a Buffer Layer in Diamond-Like Carbon Coated Artificial Hip Joints", Journal of Biomedical Materials Research, Part B: Applied Biomaterials, Jan. 1, 2003, vol. 66B, pp. 425-428.

(Continued)

*Primary Examiner* — David H Willse
*Assistant Examiner* — Javier Blanco
(74) *Attorney, Agent, or Firm* — Baker & Hostetler LLP

(57) ABSTRACT

An orthopedic implant comprising a metallic substrate coated with a diamond-like carbon (DLC) layer, and a layer of a polymeric material placed over the DLC layer that is less stiff than the substrate, and methods of manufacturing the same.

21 Claims, 2 Drawing Sheets

(51) Int. Cl.
- *A61F 2/30* (2006.01)
- *A61F 2/44* (2006.01)
- *A61L 27/04* (2006.01)
- *A61L 27/30* (2006.01)
- *A61L 27/34* (2006.01)

(52) U.S. Cl.
CPC ............... *A61F2310/00544* (2013.01); *A61F 2310/00742* (2013.01)

(56) References Cited

U.S. PATENT DOCUMENTS

| | | |
|---|---|---|
| 8,486,152 B2 | 7/2013 | Voisard et al. |
| 2005/0143824 A1 | 6/2005 | Richelsoph et al. |
| 2007/0207321 A1* | 9/2007 | Abe et al. ............ 428/413 |
| 2007/0224242 A1* | 9/2007 | Helmuth et al. ........ 424/423 |
| 2008/0154383 A1* | 6/2008 | Lechmann et al. ..... 623/18.11 |

FOREIGN PATENT DOCUMENTS

| | | |
|---|---|---|
| JP | 2003-310744 | 11/2003 |
| JP | 2005-137905 | 6/2005 |
| JP | 2007-505669 | 3/2007 |
| JP | 2007-510509 | 4/2007 |
| JP | 2008-161697 | 7/2008 |
| JP | 2008-525131 | 7/2008 |
| JP | 2008-230880 | 10/2008 |
| JP | 2010-005428 | 1/2010 |
| WO | WO 2007/086269 | 8/2007 |
| WO | WO 2007/109714 | 9/2007 |
| WO | WO 2012/005961 | 1/2012 |

OTHER PUBLICATIONS

Schwarz et al., "Thermal Stability of PIII Deposited Hard-Coatings with Compositions Between Diamond-Like Carbon and Amorphous Silicon-Carbonitride", Plasma Processes and Polymers, 2007, 4, S254-S258.

U.S. Appl. No. 61/358,968, filed Jun. 28, 2010, Voisard et al.

* cited by examiner

COATED IMPLANT

CROSS-REFERENCE TO RELATED APPLICATIONS

This application is a continuation of U.S. patent application Ser. No. 13/166,898, filed Jun. 23, 2011, now U.S. Pat. No. 8,486,152, which claims priority to Provisional Patent Application Ser. No. 61/358,968, filed Jun. 28, 2010, the disclosures of which are hereby incorporated by reference in their entirety.

BACKGROUND

1. Field of the Disclosure

The present disclosure generally relates to an implant, and in particular relates to fabricating an orthopedic implant having a resilient core.

2. Background

In order to dynamize a rigid metal-based implant, a softer elastomeric-based component is often placed between two rigid metallic elements. Such constructs have been developed for example for posterior dynamic stabilization systems for the spine or for the new generation of total disc replacements based on damping discs. In this case, a soft elastomer is set between two parallel metallic plates and provides an axial damping with motion/rotation in all six degrees of freedom.

However, bonding a soft material like an elastomer to a hard one like a metal requires careful engineering of the interfaces.

For long term implantation, a good adhesion strength under complex constant mechanical stress states is needed, and, in addition, the bond must be chemically stable (hydrolysis, oxidation). Usually, the metal surface is prepared in a manner to improve its compatibility towards a polymer. Standard methods include chemical etching using agents like chromic acid or phosphoric acid to create an optimal roughness or application of an intermediate layer, called a primer. Silane-based compositions are known as suitable primers.

Diamond-like carbon (DLC) coatings are primarily used to reduce wear or to avoid cold welding between moving parts. DLC is a typically amorphous mixture of various carbon species (sp2, sp3) with more or less hydrogen in it and some short-range graphitic or tetrahedral ordering. Because of the growth mechanisms used for DLC synthesis, these coatings typically exhibit high compressive stresses in the range of several GPa. The adhesion of DLC on a metallic substrate is thus often limiting in its use for long term application but can be stabilized with the selection of adequate interlayers. An example is an interlayer of tantalum (Ta) for CoCrMo substrates. For titanium (Ti) alloys, more sophisticated interlayers are being developed based on TaN or TaC interlayers. The surface energy of DLC can be tuned (e.g., raised) with surface treatments like exposure to an oxygen plasma or to UV light; with such processes the surface becomes either hydrophobic or hydrophilic, thus possibly improving its affinity to another material.

Elastomers are thermoplastics that can be processed by injection molding or extrusion, where granules of the raw materials are melted and pressed into a mold at a temperature higher than the melting temperature of the elastomer. The melt binds to the metallic surface to some extent. Monomers can be injected into the mold instead of the fully reacted polymers as well, in which case the polymerization happens in the mold and monomers have an additional opportunity to bind to other species present. This process is known as Reaction Injection Molding (RIM).

There remains a need for an improved implant coating.

SUMMARY

The present disclosure provides an implant including at least a first substrate, for instance a metallic substrate, having a thickness of at least 1 mm, coated with a first layer made from diamond-like carbon (DLC). The DLC layer can have a thickness as desired, such as less than 10 microns. In accordance with one embodiment, the DLC layer can have a thickness of at least approximately 500 nm. A further layer of a polymeric material can be placed over the DLC layer. The polymeric material can have a stiffness less than that of the first substrate, and can have a thickness as desired, for instance greater than 1 mm.

The polymeric material can be made from any suitable material as desired. For instance, the polymeric material can be a thermoset material or a thermoplastic, such as a thermoplastic elastomer (TPE). In accordance with certain embodiments, the polymeric material can be a polyester urethane, a polyether urethane (PEU), a polycarbonate urethane (PCU) or a polydimethylsiloxane (PDMS) containing polyurethane, which can have polar groups, such as carbonate groups. In one embodiment, the polymeric material is a silicone. The silicone materials are softer than the TPE materials.

In this regard, a relatively thin DLC layer provides an adhesion promoter that binds a surface of the first substrate with a polymeric material, such as a thermoplastic. The DLC layer can be deposited onto the surface of the first substrate, for example, via plasma activated chemical vapor deposition (PACVD) after preparing the first substrate, for instance, with a first reactive interlayer. The reactive interlayer can be made from a transition metal (including elemental transition metals and/or transition metal containing compounds or alloys). Examples of suitable transition metals include tantalum, chromium, niobium, and tungsten. Additionally or alternatively, the reactive interlayer can be made from silicon (including elemental silicon and/or silicon compounds), for example silicon carbide, in particular amorphous silicon carbide. In this regard, it should be appreciated that the reactive interlayer can be disposed between the first substrate and the DLC layer.

An outer surface of the DLC layer (i.e., a surface of the DLC layer opposite the first substrate) is activated prior to the application of the further layer. The outer surface of the DLC layer can be activated by either UV light or by exposure to a suitable plasma (oxygen, argon). Subsequently, the further layer can be processed with injection molding or reaction injection molding of the polymeric material. This interface design allows a strong and biostable material combination suitable for long-term implantation.

With the use of the DLC layer on the first substrate it is possible to achieve a chemical bond with the polymeric material of the further layer and thus raise the adhesion strength with the first metallic substrate.

Usual adhesion promotion techniques often include the use of non biocompatible substances like acids that require a careful management of part cleaning and process safety. On the other hand, the long-term use and effects of standard primers like silane are not known for the human spine. For total disc replacement devices, an adhesion strength under severe conditions is desired for long-term deployment. The interfaces are typically subjected to hydrolysis/oxidation attacks and high dynamic mechanical stresses. The DLC layer improves the adhesion strength and renders the implant system biostable.

Processing the implant including the first substrate and the DLC layer happens under controlled conditions with physical/chemical vapor deposition, lowering the risk of erroneous processing. Further enhancements of process control are possible by in-situ diagnostics like mass spectrometry.

The implants according to the present disclosure offer advantages of a high link density, chemical inertness and mechanical strength.

The first metallic substrate can be made from a CoCr alloy, stainless steel, titanium or a titanium alloy. The hydrogen content and predominant bonding type of the DLC layer can be configured as desired. For instance, the DLC can be mainly tetrahedrally bonded with low atomic hydrogen concentrations to provide dense chemical linking to hydrocarbons, high adhesion strengths to metals, chemical inertness in bulk form and mechanical strength. Alternatively, the DLC can have greater hydrogen concentration that can provide higher elasticity to accommodate the mechanical properties of the bonded elastomers. For example, the hydrogen concentration in the DLC layer can vary between substantially 0 and about 35 atomic percent.

In accordance with one embodiment, the tetrahedral amorphous DLC has a hydrogen content as desired. For instance, the DLC can have a hydrogen content of zero or substantially zero, for instance, less than approximately 1 atomic percent, thereby providing a particularly hard DLC layer. The hydrogen content of the tetrahedral amorphous DLC can be raised to a higher amount, which provides a relatively soft DLC layer. According to one embodiment, the hydrogen content can be at least about 25 atomic percent, and in another embodiment, the hydrogen content can be in the range of about 25 to about 35 atomic percent. Thus, the hardness of the DLC layer decreases as the hydrogen content increases. Further, the DLC layer can have a hydrogen content anywhere in a range of 0 to about 35 atomic percent so as to control the hardness of the DLC layer, and can have a variable content gradient of hydrogen along a direction between the first substrate and the further layer. Accordingly, the substrate-facing portion of the DLC layer can have a first hydrogen content, and the further layer-facing portion of the DLC layer can have a second hydrogen content that is equal to or different than (for instance greater than or less than) the first hydrogen content. Thus, the portions of the DLC layer can be configured to have respective mechanical properties (e.g., hardness) that accommodate and take advantage of the mechanical properties of adjacent elements at the interfaces. The adjacent element can be the first substrate or the polymeric material of the further layer, the first reactive interlayer between the first substrate and the DLC layer, or alternatively can be a first primer interlayer disposed between the DLC layer and the further layer. The primer interlayer serves to increase the bonding characteristics between the DLC layer and the polymeric material. For example, silane-based compositions are useful as a primer interlayer.

It should be appreciated that the hydrogen content can gradually increase in a direction from the first substrate towards the further layer. The hydrogen content can be measured using a standard procedure like ERD (elastic recoil detection).

It should be further appreciated that the DLC layer can be doped with fluorine or nitrogen, thereby influencing the surface energy of the DLC layer. Surface energy can be determined by several factors that pertain to the wetting behavior of various liquids, for example, monomer liquids that comprise base units of the polymeric material that is applied as the further layer to the DLC layer after doping. Thus, the doping of the DLC layer can have different effects depending upon the characteristics of the selected liquid. Accordingly, doping the DLC layer and altering the surface energy of the DLC layer can provide an improvement to the desired wetting behavior. For example, fluorine doping of the DLC layer can effectively lower the surface energy at an interface where the DLC layer interacts with a polar liquid monomer resulting in a more hydrophobic monomer, whereas the same polar monomer can become more hydrophilic in the presence of a nitrogen doping and surface activation with oxygen and nitrogen. In accordance with one embodiment, the doping step can be achieved by doping the DLC layer with elements such as nitrogen or silicon via addition of relevant precursor gases during an acetylene deposition step.

In a further embodiment, the implant can include a second substrate that can be constructed as described above with respect to the first substrate. Thus, the second substrate can be coated with a second DLC layer, and a second reactive interlayer can be disposed between the second substrate and the second DLC layer in the manner described above with respect to the first substrate and the first reactive interlayer. The further layer of polymeric material described above can also be placed over the second DLC layer such that the further layer is disposed and connected between the first and second substrates.

In accordance with certain embodiments, the implant is an intervertebral implant having a first and a second substrate, each adapted to contact endplates of two adjoining vertebrae, respectively. In this regard, the first and second substrate of the intervertebral implant can provide the first and second substrates that are coated in the manner described above.

The intervertebral implant extends along a central axis. For instance, the intervertebral implant includes a first bone-contacting plate and a second bone-contacting plate that are spaced apart along the central axis. The intervertebral implant further includes a resilient core disposed between said first and second bone-contacting plates. Accordingly, the first bone contacting plate can define a first substrate coated with a first DLC layer, the second bone contacting plate can define a second substrate coated with a second DLC layer, and the resilient core can comprise the further layer of polymeric material disposed between the first and second DLC layers. The resilient core may comprise a single layer or multiple layers. For example, the resilient core may comprise several layers of different hardness (e.g., from hard to soft), to, for example, ease the transition from the metallic substrate to the polymeric material. The resilient core may also comprise various additives that provide different functions, e.g., barium sulfate for radioopacity, silver or silver ions for antibacterial effect, and/or hydroxyapatite for osseointegration. The layers of the resilient core may also vary in porosity, with increased porosity being able to improve osseointegration to the extent bone can grow into the pores.

In accordance with one embodiment, the first bone-contacting plate defines a first internal locking member and said second bone-contacting plate defines a second internal locking member. The first and second internal locking members can form an interlocking structure that allows limited displacement and rotation of the first and second bone-contacting plates relative to each other. It should be appreciated that the interlocking structure increases the contacting surface between the first and second bone-contacting plates and the resilient core. The interlocking structure thus limits deformation of the resilient core when the first and second bone-contacting plates become displaced from each other in a direction having directional components that extend both parallel and orthogonal with respect to the central axis of implant. The interlocking structure can also limit deformation of the resilient core when the first and second bone-contacting plates rotate relative an axis that is angled (for instance orthogonal) with respect to the central axis. The interlocking structure prevents the resilient core from being deformed to a too large extent.

In a further embodiment of the implant said resilient core can have a Young's modulus of 5-50 MPa, preferably 10-20 MPa.

In accordance with one embodiment, a method of manufacturing the implant can include the following steps of:
a) ultrasonically cleaning a substrate, for instance, in an organic solvent;
b) inserting the cleaned and dried substrate into a vacuum system, which can, for example, be pumped to a base pressure of approximately $10^{-7}$ mbar;
c) precleaning of the substrate, for instance, using an argon bombardment, which can, for example, be carried out at approximately $2 \cdot 10^{-2}$ mbar;
d) depositing of a DLC layer onto the precleaned substrate. The DLC layer can have a thickness as desired, for instance, less than approximately 10 microns. The DLC layer can be deposited onto the substrate by any suitable deposition technique, such as deposition from acetylene; and
e) placing a further layer of polymeric material onto the DLC layer. The polymeric material can have a stiffness as desired, for instance, less than that of the substrate. The further layer can have a thickness as desired, such as greater than 1 mm.

It should be appreciated that the various layers can be placed directly onto or over each other, or indirectly placed onto or over each other via an intermediate layer as desired.

In accordance with one embodiment, a reactive interlayer of a silicon or metallic compound can be deposited onto or over the precleaned substrate, for instance by tetramethylsilane deposition or magnetron sputtering. The DLC layer can then be deposited onto or over the reactive interlayer. In this regard, it should be appreciated that the DLC layer is deposited onto or over the precleaned substrate via an intermediate layer which is provided as the reactive interlayer.

In another embodiment of said method, the metallic compound is Ta, Cr, Nb, W or Ti.

In a further embodiment, a primer interlayer can optionally be disposed at the interface of DLC layer and the resilient core.

The bonding technology disclosed herein may be used in applications where binding a metal to a polymer is required or desired. In addition to the specific embodiments described herein, such uses may include a posterior dynamic stabilization rod made of metallic and elastomer components, a finger joint prosthesis, a fusion device for the lumbar spine or for facet joints, and instruments with a compliant soft component and metallic stiff parts. The bonding technology described herein provides, for example, increased flexibility, mobility and/or shock absorption, while still allowing enough stability as required for an implant.

DESCRIPTION OF THE DRAWINGS

The foregoing summary, as well as the following detailed description of embodiments of the application, will be better understood when read in conjunction with the appended drawings. For the purposes of illustrating the present invention of the present application, there is shown in the drawings preferred embodiments. It should be understood, however, that the application is not limited to the precise arrangements and instrumentalities shown. In the drawings.

DETAILED DESCRIPTION

Figure 1:
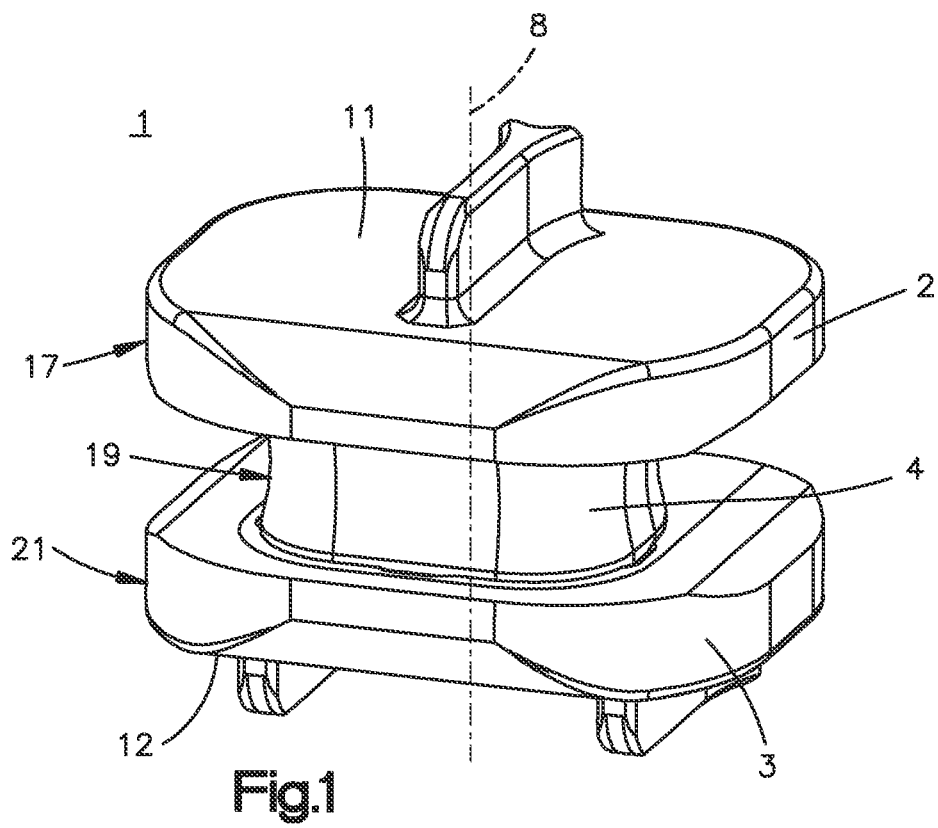
FIG. 1 is a perspective view of an implant constructed in accordance with one embodiment.
Figure 2:
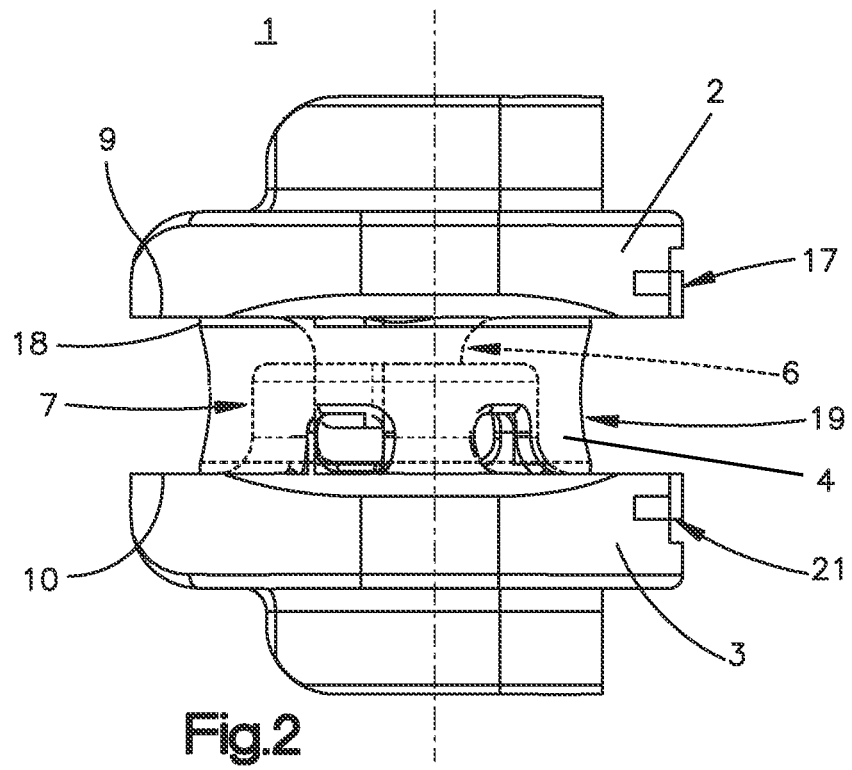
FIG. 2 is a side elevation view of the implant illustrated in FIG. 1.
Figure 3:
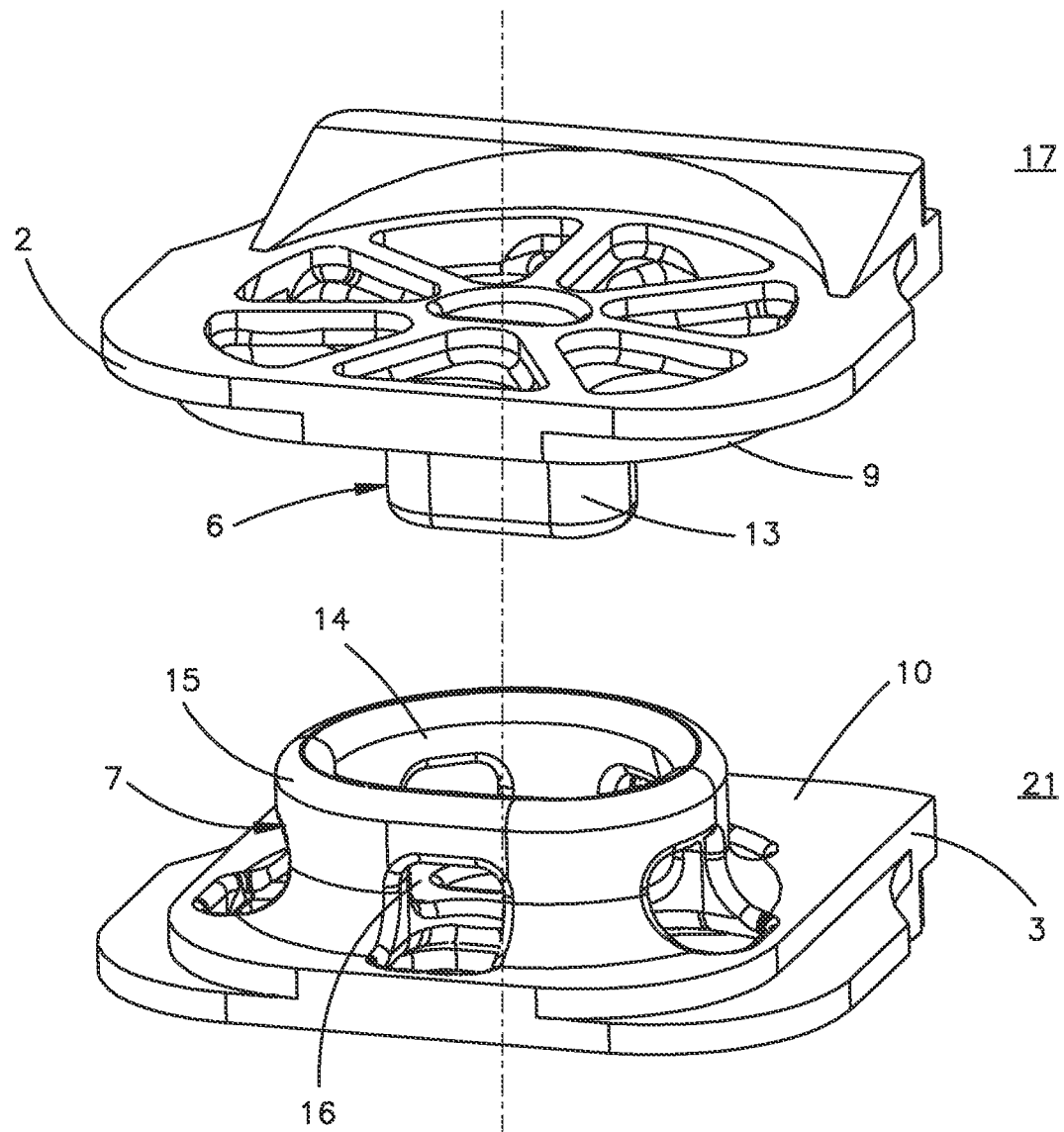
FIG. 3 is an exploded perspective view of the implant illustrated in FIG. 1 having a portion cut away for the purposes of illustration.

Referring to FIGS. 1-3, an orthopedic implant 1 is configured as an intervertebral implant 1, and extends along a central axis 8 and further extends in a direction transverse to the central axis 8. The implant 1 includes a first substrate 17 that, in turn, includes a first bone contacting plate 2 and a first internal locking member 6. The implant 1 further includes a second substrate 21 that, in turn, includes a second bone contacting plate 3 and a second internal locking member 7 that engages the first internal locking member 6. The implant 1 further includes a resilient core 4 disposed between the first and second bone contacting plates 2 and 3. The resilient core 4 can provide a dampening member during operation of the implant 1. The first and second bone contacting plates 2 and 3 can be made from titanium, a titanium alloy, e.g. Ti6Al7Nb, or any alternative suitable biocompatible material, such as a CoCr alloy, stainless steel, or any alternative metal as desired. It should be further appreciated that the first and second contacting plates can define regions that provide the first 17 and second 21 substrates onto which a DLC layer is deposited.

The first bone contacting plate 2 defines a first outer bone contacting surface 11 and a second inner facing surface 9. The outer bone contacting surface 11 is configured to contact a lower end plate of an adjacent vertebral body. The inner facing surface 9 faces the second bone plate 3. The second bone contacting plate 3 likewise has a first outer bone contacting surface 12 and a second inner facing surface 10. The outer bone contacting surface 12 is configured to contact an upper end plate of an adjacent vertebral body. The inner surface 10 faces the first bone contacting plate 2. The resilient core 4 can be made from any suitable material that provides damping characteristics as desired. For instance, the resilient core 4 can comprise the further layer 19 as described herein. For example, the resilient core 4 material may be selected from a group of segmented polyurethane copolymers, such as a polyurethane-based thermoplastic elastomer (TPE) or a silicone material or silicone.

The first internal locking member 6 extends from the inner surface 9. Likewise, the second internal locking member 7 extends from the inner surface 10. In accordance with one embodiment, the first internal locking member 6 can be integral with the inner surface 9, and the second internal locking member 7 can be integral with the inner surface 10. It should be appreciated, however, that the locking members 6 and 7 can alternatively be discretely connected to the respective inner surfaces 9 and 10. The first and second interlocking members 6 and 7 can combine to provide an interlocking structure of the implant 1.

The intervertebral implant 1 therefore includes:
a first substrate 17, which includes said first bone contacting plate 2 and said first internal locking member 6;
a first DLC layer 18 having a thickness of less than 10 microns which is placed over said inner surface 9 of said first bone contacting plate 2 and the surface of said first internal locking member 6;

a resilient core 4 comprising a further layer 19 of a polymeric material disposed between said first and second bone contacting plates 2, 3;

a second substrate 21, which includes said second bone contacting plate 3 and said second internal locking member 7; and a second DLC layer 18 having a thickness of less than 10 microns which is placed over said inner surface 10 of said second bone contacting plate 3 and the surface of said second internal locking member 7.

In this regard, the first DLC layer 18 is disposed between the resilient core 4 and the first substrate 17, while the second DLC layer 18 is disposed between the resilient core 4 and the second substrate 21. Furthermore, a primer interlayer can be disposed between the first DLC layer 18 and the further layer 19 as well as between the second DLC layer 18 and the further layer 19. The primer interlayer can promote bonding (e.g., chemical and/or mechanical) between the DLC layers 18 and the respective polymeric material of the further layer 19. The primer interlayer can be formed for example by a silane such as gammamethacryloxypropyltrimethoxysilane (Primer A-174).

Attaching the DLC layer 18 to the metallic substrates 17, 21 of said first and second bone contacting plate 2, 3 promotes a chemical bond between the polymeric material of the resilient core 4 and said first and second bone contacting plate 2, 3 thus raising the adhesion strength of resilient core 4 with the metallic substrate of said first and second bone contacting plate 2, 3.

The first internal locking member 6 is configured as a first protrusion forming a peg 13 projecting from the inner surface 9 of said first bone contacting plate 2. The peg 13 can define an oval cross-sectional area along a direction orthogonal to the central axis 8. The peg further extends coaxially with the central axis 8. The second internal locking member 7 is configured as a second protrusion extending from the inner surface 10 of the second bone contacting plate 3. The second protrusion can define an oval recess 14 that extends coaxially with the central axis 8. Thus, the second internal locking member 7 defines an annular wall 15 that defines the oval recess 14. The oval recess 14 has an oval cross-sectional area along a direction orthogonal to the central axis 8. The cross-sectional area of the oval recess 14 is greater than the cross-sectional area of said peg 13, such that a spacing transverse to the central axis 8 remains when said peg 13 is received within said oval recess 14. Due to said spacing, the interlocking structure allows the first and second bone-contacting plate 2 and 3 to displace and rotate relative to each other. The possible relative motion between the first and second bone contacting plates 2 and 3 is limited by the interlocking structure to a range of approximately 0 mm to approximately 2 mm, such as approximately 1 mm. Furthermore, the interlocking structure increases the contacting surface between each of the first and second bone contacting plates 2 and 3 and the resilient core 4. Additionally, the annular wall 15 of the second internal locking member 7 can include a plurality of perforations 16 so that the polymeric material of the resilient core 4 can penetrates through the perforations 16 into said spacing between the peg 13 and said inner surface 15, thereby providing for improved fixation of said resilient core 4 to the second bone contacting plate 3.

Manufacture

The surface of the DLC layer 18 to which the polymer material of the further layer 19 is bonded can be subjected to an activation treatment, which can be performed shortly before the further layer 19 is bonded to the DLC layer 18, thereby avoiding decay. The activation treatment removes contaminants from the surface of the DLC layer 18 and creates dangling bonds on the DLC layer 18 surface that are suitable for connections with the polymer material of the further layer 19. The activation treatment can be accomplished using a process such as exposure of the surface of the DLC layer 18 to an atmospheric pressure plasma (e.g. oxygen, air, argon, or the like) or to short-wavelength UV radiation. The activation treatment can be carried out so as to avoid significant graphitization of the surface. The polymeric material of the further layer 19 can be a thermoplastic elastomer (e.g. a polydimethylsiloxane-based segmented polyurethane) or a thermoset material. Prior to application of the DLC layer 18, the substrate 17, 21 surface can be structured to gain an additional increase in adhesion due to surface geometry effects.

Example

Elastomeric Dampening Element

It should thus be appreciated that a biostable metal-elastomer link can be provided that is capable of withstanding dynamic loading in-vivo, for instance when included in an intervertebral implant. Such links are desirable to connect osseointegrative plates (e.g. surface treated TiAlNb alloy) to a dampening element for joint replacements (spinal disks, finger joint prosthesis, etc.).

The DLC layer 18 can be fabricated by plasma assisted chemical vapor deposition (PACVD) using an acetylene plasma, so as to deposit the DLC layer 18 onto the substrates 17 and 21. A stable connection (TiAlNb base plate—DLC) can be attained by using an appropriate reactive interlayer system in the coating process. Compositions suitable as the reactive interlayer can include silicon such as elemental silicon or silicon compounds such as silicides. Alternatively or additionally, the reactive interlayer can be made from tantalum, including elemental tantalum, and tantalum compounds, such as tantalum carbide and tantalum nitride. This process of depositing the DLC layer 18 onto the substrate can be described as follows:

1. ultrasonic cleaning of the plates in an acetone/ethanol mixture;
2. inserting the cleaned and dried plates into a vacuum system and pumping to a base pressure of, for example, $10^{-7}$ mbar;
3. precleaning the plates by argon bombardment at, for example, $2 \cdot 10^{-2}$ mbar with −600V RF (radio frequency) self-bias for 30 min;
4. depositing a 100 nm silicon interlayer by tetramethylsilane deposition at, for example, −600V RF self-bias for 10 min; and
5. depositing a 500 nm thick DLC layer by deposition from acetylene at an RF self-bias of, for example, −600V for 15 min.

Prior to attaching the further layer to the DLC layer, the DLC layer can be activated in the manner described above. The activation removes surface contaminants and polarizes the surface of the DLC layer by hydrogen removal and oxygen attachment, thus raising the surface energy of the DLC layer. Accordingly, the DLC surface has a high density of docking sites for subsequent attachment of the polymeric material of the further layer. The plasma activation process can be described as follows:

1. preclean the samples by ultrasound in an acetone/ethanol mixture for 5 minutes;

2. dry the samples in an inert gas jet and place them in a vacuum chamber capable of base pressure $<1\cdot10^{-4}$ mbar;
3. apply a plasma (argon, oxygen or nitrogen) of ion density $1\cdot10^{10}/cm^3$ by ECR (electron-cyclotron resonance), RF or similar to the DLC layer for at least 20 minutes. The ion energy at the sample surface should not cause significant sputtering and the samples should not heat up significantly; and
4. remove samples from the vacuum chamber and mold them no later than 20 minutes after the plasma activation treatment.

Once the surface of the DLC layer has been activated, the further layer is attached to the DLC layer, for instance via injection molding. In accordance with one embodiment, the further layer can be attached to the DLC layer via reactive injection molding (RIM).

In an alternative embodiment to the above described plasma activation, the DLC layer can also be activated using UV light or electron beam activation. In such a UV light activation, process step 3 can be described as follows:
3. apply high intensity UV radiation having an energy greater than 4.5 eV to the DLC layer for at least 10 minutes.

In such an electron beam activation, process step 3 can be described as follows:
3. apply an electron beam having an energy greater than 4.5 eV to the DLC layer for at least 10 minutes.

Although present embodiments have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

The invention claimed is:

1. An orthopedic implant comprising:
 a first bone contacting plate including:
  a first metallic substrate;
  a first diamond-like carbon (DLC) layer coated onto the first metallic substrate; and
 a second bone contacting plate including:
  a second metallic substrate; and
  a second diamond-like carbon (DLC) layer coated onto the second metallic substrate; and
 a resilient core comprising a resilient polymeric material bonded to the first and second DLC layers so as to join the first and second bone contacting plates, the resilient core disposed between the first and second bone contacting plates;
 wherein the first DLC layer is made of an amorphous DLC, wherein the first DLC layer has a hydrogen content between 0 atomic % and about 35 atomic %, and wherein the first DLC layer has variable hydrogen content gradient, and wherein the hydrogen content increases in a direction from said first substrate towards said resilient core.

2. The implant according to claim 1, wherein the first substrate is made from a CoCr alloy, stainless steel, titanium or a titanium alloy.

3. The implant according to claim 1, wherein the first DLC layer has a thickness of at least about 500 nm.

4. The implant according to claim 1, wherein the first DLC layer is made of tetrahedral amorphous DLC.

5. The implant according to claim 1, wherein the first DLC layer has a hydrogen content of less than about 1 atomic %.

6. The implant according to claim 1, wherein the first DLC layer has a hydrogen content of at least about 25 atomic %.

7. The implant according to claim 1, wherein the first DLC layer has a hydrogen content in the range of about 25 atomic % to about 35 atomic %.

8. The implant according to claim 1, wherein the first DLC layer is doped with fluorine or nitrogen.

9. The implant according to claim 1, wherein said polymeric material is a thermoplastic elastomer (TPE).

10. The implant according to claim 1, wherein said polymeric material is a polyester urethane, a polyether urethane (PEU), a polycarbonate urethane (PCU) or a polydimethylsiloxane (PDMS) containing polyurethane.

11. The implant according to claim 10, wherein said polydimethylsiloxane (PDMS) containing polyurethane has polar groups.

12. The implant according to claim 1, wherein said polymeric material is a silicone material.

13. The implant according to claim 1, wherein the first and second DLC layers each have a thickness of less than 10 microns.

14. The implant according to claim 1, wherein said first bone contacting plate comprises a first internal locking member and said second bone contacting plate comprises a second internal locking member and wherein said first and second internal locking members form an interlocking structure configured to allow a limited displacement and rotation of the first and second bone contacting plate relative to each other.

15. The implant according to claim 1, wherein said resilient core has a Young's modulus of 5-50 MPa.

16. The implant according to claim 15, wherein the resilient core has a Young's modulus of 10-20 MPa.

17. A method for manufacturing the implant according to claim 1 comprising:
 a) precleaning of the first substrate;
 b) depositing the first DLC layer on the first substrate; and
 c) applying the resilient polymeric material over the first DLC layer.

18. The method according to claim 17, further comprising depositing a reactive interlayer between steps b) and c), wherein the reactive interlayer is a silicon or metallic containing compound.

19. The method according to claim 18, wherein the metallic containing compound is selected from the group consisting of Ta, Nb, W, Ti, and mixtures and alloys thereof.

20. The orthopedic implant of claim 1, further comprising a first reactive interlayer disposed between the first metallic substrate and the first DLC layer, and a second reactive interlayer disposed between the second metallic substrate and the second DLC layer, the reactive interlayers configured to promote bonding between the first and second DLC layers and the first and second substrates, respectively.

21. The orthopedic implant of claim 1, further comprising a primer interlayer disposed between the first DLC layer and the resilient core.

* * * * *